United States Patent [19]

Wiley

[11] Patent Number: 5,066,301

[45] Date of Patent: Nov. 19, 1991

[54] VARIABLE FOCUS LENS

[76] Inventor: Robert G. Wiley, 4545 Brookside Rd., Toledo, Ohio 43615

[21] Appl. No.: 594,086

[22] Filed: Oct. 9, 1990

[51] Int. Cl.$^5$ .................. A61F 2/16; G02B 26/00; G02C 7/04; G02C 7/02

[52] U.S. Cl. .................. 623/6; 351/160 H; 351/161; 351/176; 359/94

[58] Field of Search .................. 623/4-6; 350/347 V, 362; 351/160 H, 161, 176

[56] References Cited

U.S. PATENT DOCUMENTS

| | | | |
|---|---|---|---|
| 4,277,852 | 7/1981 | Poler | 623/6 |
| 4,298,996 | 11/1981 | Barnet | 623/6 |
| 4,373,218 | 2/1983 | Schachar | 623/6 |
| 4,512,039 | 4/1985 | Lieberman | 623/6 |
| 4,564,267 | 1/1986 | Nishimoto | 350/329 |
| 4,575,373 | 3/1986 | Johnson | 623/6 |
| 4,601,545 | 7/1986 | Kern | 350/347 V |
| 4,601,722 | 7/1986 | Kelman | 623/6 |
| 4,787,903 | 11/1988 | Grendahl | 623/6 |
| 4,816,031 | 3/1989 | Pfoff | 623/6 |

Primary Examiner—Ronald Frinks
Attorney, Agent, or Firm—Marshall & Melhorn

[57] ABSTRACT

A variable focus lens apparatus includes a transparent, generally circular envelope, a transparent gel having a relatively high resistance to flow encased in the envelope, and a plurality of light refractive particles suspended in a predetermined orientation in the gel. When an external force field is applied to the lens apparatus, the selectively focusable particles are responsive for changing to a new orientation with respect to said envelope for selectively adjusting characteristics of the lens apparatus including at least one of the characteristics of power and astigmatism correction, whereby upon removal of the external force, the particles remain in the new orientation within the gel. A control system for controlling at least one of the strength and duration of the force field applied to the particles is connected to coils and a power supply for generating the force field.

20 Claims, 4 Drawing Sheets

VARIABLE FOCUS LENS

BACKGROUND OF THE INVENTION

The present invention relates generally to a variable focus lens and, in particular, to an apparatus for varying the power of and providing astigmatism correction in an intraocular lens.

The lens of the human eye is located centrally behind the pupil and is protected by the cornea. In the normal eye, the lens is clear and is substantially symmetrical, with opposed convex surfaces defining generally spherical sections. The lens and the cornea cooperate to focus light on the retina. The retina in turn cooperates with the nerves and the brain, so that light impinging on the retina is perceived as an image.

The light refraction which takes place in the cornea and the lens translates into an optical correction of about 60 diopters, with the cornea accounting for about 40 diopters and the lens accounting for about 20 diopters. Other refracting structures also are present in the eye, but are disregarded to simply the subject explanation.

A cataract is a condition where the normally clear lens of the eye becomes progressively opaque. This opacification typically occurs over an extended period of time, and the amount of light which passes through the lens decreases with increasing degrees of opacity. As the ability of the cataract lens to transmit light decreases, the ability of the eye to perceive images also decreases. Blindness ultimately can result. Since there are no known methods for eliminating the opacity of a cataract lens, it generally is necessary to surgically remove the opaque lens to permit the unobstructed passage of light through the pupil to the retina. The cataract lens is removed through a generally horizontal incision made at the superior part of the juncture where the cornea and sclera meet.

Once the lens has been surgically removed, light can be readily transmitted through the pupil and toward the retina.

As noted above, the lens of the eye performs a significant light focusing function. Consequently, with the lens removed, the optical system of the eye is left about 20 diopters "short" and light is no longer properly focused on the retina. Eyeglasses, contact lenses and intraocular lenses are the three types of optical aids that commonly may be employed after cataract surgery to refocus the light on the retina.

Eyeglasses include lenses which are spaced from the cornea of the eye. The air space between the lens and the cornea causes an image magnification of more than 7%. Unfortunately, the brain cannot assimilate this magnification in one eye, and as a result an object appears double. This is a particular problem if the individual had only one cataract eye. Eyeglasses also substantially limit peripheral vision.

Contact lenses rest directly on the cornea of the eye, thus eliminating the air space. As a result, there is a much smaller image magnification with contact lenses than there is with eyeglasses, and the brain typically can fuse the images perceived by an eye with a contact lens and one without. Contact lenses, however, are less than perfect. For example, contact lenses are quite fragile and can be easily displaced from their proper position on the cornea. Additionally the lenses must be periodically replaced because of protein build-up on the surface of the lens which can cause conjunctivitis. Furthermore, many of the elderly people who require cataract operations do not have the required hand coordination to properly remove or insert the lens.

Intraocular lenses first because available as optical aids to replace removed cataract lenses in about 1955. These lenses are placed in the eye, and thus closely simulate the optics of the natural lens which they are replacing. Unlike eyeglasses, there is virtually no image distortion with a properly made and placed intraocular lens. Also unlike contact lenses, there is no protein build-up on the intraocular lenses and the lenses require no care by the patient.

To place the lens in the eye, the surgeon ordinarily makes an incision or opening in the cornea which aligns with the pupil, and the surgeon passes the lens through the opening. The attachment members of the lens are flexible and can be bent to pass through the opening. Accordingly, the minimum length of opening which must be made and is ordinarily determined by the diameter of the substantially rigid lens body, or optic, usually having a circular periphery. It is, of course, desirable to make the opening in the cornea as small as possible to minimize the risk of damage to the eye.

The current practice in the implantation of intraocular lenses is to replace a normal crystalline human lens of the eye removed at the time of surgery, such as in cataract surgery, with an intraocular lens such as an anterior chamber lens or posterior chamber lens formed of PMMA (polymethyl methacrylate) material. However, one of the present problems with intraocular lenses is that it is necessary to decide on the power of the lens preoperatively. This can be accomplished, for example, by performing an ultrasound scan and/or evaluating the patient's refraction preoperatively and then making a clinical estimate of the proper power of the lens in order to determine proper refraction of the eye. However, even with the best medical techniques and sophisticated optical instruments available, ophthalmologists have never been able to correct for accommodation of vision from distance to near vision and the power of the lens implant is seldom accurate enough for the patient to function without the use of glasses for accurately focused distance and near vision.

The prior art intraocular lens typically is either of plano-convex construction or double convex construction, with each curved surface defining a spherical section. The lens is placed in the eye through the same incision which is made to remove the cataract lens. As noted above, this incision typically is made along the superior part of the eye at the juncture of the cornea and the sclera. About one third of all postoperative patients will have significant astigmatism and, approximately one third will need a spherical adjustment in their postoperative glasses to see clearly. In virtually all instances, the surgery itself induces astigmatism which fluctuates significantly during the first few weeks, or even months, after the surgery.

Postoperative induced astigmatism is attributable to the healing characteristics of the eye adjacent the incision through which the cataract lens is removed and the intraocular lens is inserted. More particularly, the sutured incision in the eye tends to heal more slowly and less completely as compared to incisions in the skin. For example, a sutured incision in skin typically heals in five to seven days, whereas a comparable incision in the eye may take eight weeks to a year to properly heal depending on the method of suturing. This slow healing rate is attributable to the nature of the eye tissue, poor vascularity and topical cortisone use after surgery. During the period when the eye is healing, the sutured area tends to spread and thus as cornea that may have been spherical before surgery is made other than spherical. Since the incision is generally horizontally aligned, the spreading is generally along the vertical meridian. Consequently, the optical system of the eye, which may previously have been spherical, becomes "toric" with the vertical meridian of the optical system providing a different optical power than the horizontal meridian. This non-spherical configuration of the optic system is generally referred to as "astigmatism".

The degree of this induced astigmatism varies according to the type of sutures used, the suturing technique and the technical skill and care employed by the surgeon, and the physical attributes of the eye. For example, the use of a fine nylon suturing material typically results in a smaller deviation from sphericity than the use of silk or absorbable suture. Generally, the induced astigmatism varies from 0.5 to 5 diopters. Although, the astigmatism resulting from the operation is generally caused by the steepening of the vertical meridian, the orientation and amount of deviation are not accurately predictable. Postoperative astigmatism typically is corrected by prescription eyeglasses which need to be changed periodically as the eye heals.

In some cases, despite the best efforts of the ophthalmologist, the lens surgically placed in the patient's eye does not provide good distance visual acuity due to spherical miscalculations and changing astigmatic requirements. Since the surgery itself can cause significant change in the amount and axis of the astigmatism present after cataract surgery, the exact amount and axis of astigmatism can not be accurately determined until sometime usually several weeks, after the surgery. Since the old intraocular lens can not be readily removed and a new intraocular lens with a different power surgically installed without unduly jeopardizing the patient's vision, the patient must rely on spectacles to provide accurately focused visual acuity. In other words, although the need to wear heavy, bulky, higher power spectacles is eliminated, the patient nevertheless usually must wear spectacles for good vision.

Several attempts have been made to provide a variable power intraocular lens, which power varies according to an application of a force external to the lens, for correcting the astigmatism expected after surgery. U.S. Pat. No. 4,787,903 discloses an intraocular lens including an annular Fresnel (prism) lens, made of a high index of refraction material such as polymethylmethacrylate. A composite material overlays the Fresnel elements to provide a smooth external surface and is made of a suitable material, for example, crystalline lattice or liquid crystal material, which changes the index of refraction when excited with electrical power or radiant energy. The lens carries a complementary loop or other energy pick-up device, for receiving the power from an electric field generated by an external power source feeding a coupling loop. The coupling loop can be carried in an eyeglass frame, implanted about the eye socket or positioned by the lens wearer or an ophthalmologist. It is stated in the patent specification that some overlay materials can be switchable between more than two states, each with a different index of refraction, while other materials will provide a continuously variable index of refraction which may be stable or may return to an initial value when the energy is removed. However, such materials are not identified in the patent.

U.S. Pat. No. 4,601,545 discloses a variable power lens system including an optically active molecular material such as liquid crystals. A variable gradient index of refraction is achieved by applying a controlled stimulus field, such as a geometrically configured matrix of electrical voltages, to the lens. A corresponding matrix of horizontal and vertical conductors applies the electrostatic field produced by the applied voltage to be selectively controlled at discrete points so that a gradient index of refraction is produced.

U.S. Pat. No. 4,564,267 discloses a variable focal length lens which can be electrically controlled by applying an electric field to a compound lens including at least one lens formed of electrooptic crystals. The electrooptic crystals are juxtaposed between first and second transparent electrode plates each comprising a plurality of concentric annular transparent electrodes. A power source connected to the electrodes generates an electric field across the crystals creating a refracting index distribution having a lens action. The electric field effectuates a change in the focal length of the lens which varies according to the potential imparted.

U.S. Pat. No. 4,373,218 discloses a variable power intraocular lens including a fluid expandable sac for containing a liquid crystal material that is used in combination with an electrode and a microprocessor for changing the index of refraction of the lens. An electrode is located in a ciliary body to provide an input signal that is proportional to a desired accommodation to a microprocessor which can be implanted into a sclera of a human eye. The microprocessor produces a potential across the liquid crystal material to control the index of refraction to obtain the desired accommodation based upon the relative position of the eyes. The voltage output of the microprocessor is applied to electrodes which can be a thin transparent material forming a coating on the interior of the fluid expandable sac.

SUMMARY OF THE INVENTION

The present invention concerns a variable focus lens which can be formed as an intraocular lens implanted in the human eye. The lens has other applications including use in a camera.

The variable focus lens according to the present invention has a transparent envelope formed of plastic or the like encasing a transparent gel made of a suitable material having a high viscosity such as silicone, for example, in which light refracting particles are suspended. However, the envelope can also be a skin or outer layer of the gel material with can hold the shape of the lens. The physical and electrical properties of the gel maintain the refracting particles in a fixed position in the gel. The particles are composed of a suitable material which is responsive to an external force for rotating or changing the orientation of the particles in position within the gel. Thus, as the orientation of the particles is changed, there is a change in the refracting index of the lens, so that the spherical and/or astigmatic correction of the lens can be added or subtracted by the selective rotation or alignment of the refracting particles.

An external electromagnetic force or other suitable source of energy is applied to adjust the lens until it is properly focused. The gel, having a high resistance to flow, maintains the particles in a changed position after the external force is removed.

In an intraocular lens application, the vision of the lens implant recipient may be corrected to perfect or near perfect vision. The changed power and/or astigmatism correction of the lens remains stable until such time the implant recipient needs to have the external force field applied to correct a deviation from perfect vision caused by other sources thus eliminating the need for changes in glasses to keep the eye in good focus. Furthermore, the lens according to the present invention is stable, retaining the focus and/or astigmatism correction after the external force field has been removed. Such lens does not require a continuous power source, nor a power source being coupled to the lens material by circuitry and a matrix of electrodes, nor power coupling loops to supply continuous power to the lens.

BRIEF DESCRIPTION OF THE DRAWINGS

The above, as well as other advantages of the present invention, will become readily apparent to those skilled in the art from the following detailed description of a preferred embodiment when considered in the light of the accompanying drawings in which.

DESCRIPTION OF THE PREFERRED EMBODIMENT

Figure 1:
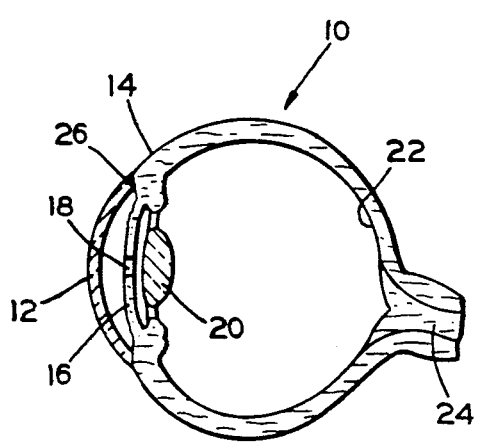
FIG. 1 is a cross-sectional side elevation view of a normal human eye prior to removal of the natural lens.

Referring to the FIG. 1, there is illustrated a normal human eye generally indicated by the reference numeral 10. The eye 10 includes a cornea 12 covering an opening in a generally spherical sclera 14. Positioned interiorly of the cornea 12 in the opening in the sclera 14 is an iris 16 having a pupil 18. Positioned behind the pupil 18 is a lens 20 which focuses entering light onto a retina 22 on the interior surface of the eye, the retina being connected to the brain (not shown) by an optic nerve 24. The lens 20 is located centrally behind the pupil 18 and is protected by the cornea 12. In the normal eye 10, the lens 20 is clear and is substantially symmetrical, with opposed convex surfaces defining generally spherical sections. The lens 20 and the cornea 12 cooperate to focus incoming light on the retina 22. The retina 22 in turn cooperates with the optic nerve 24 and the brain, so that light impinging on the retina 22 is perceived as an image.

The light refraction which takes place in the cornea 12 and the lens 20 translates into an optical correction of about sixty diopters, with the cornea 12 accounting for about forty diopters and the lens 20 accounting for about twenty diopters. Other refracting structures also are present in the eye 10, but are disregarded here to simplify the explanation.

A cataract is a condition where the normally clear natural lens 20 of the eye 10 becomes progressively opaque. This opacification typically occurs over an extended period of time, and the amount of light which passes through the lens 20 decreases with increasing degrees of opacity. As the ability of the cataract lens 20 to transmit light decreases, the ability of the eye 10 to perceive to images also decreases. Ultimately, blindness can result. Since there are no known methods for eliminating the opacity of a cataract lens 20, it generally is necessary to surgically remove the opaque lens 20 to permit the unobstructed passage of light through the pupil 18 to the retina 22. The cataract lens 20 is removed through a generally horizontal incision made at the superior part of a juncture 26 where the cornea 12 and the sclera 14 meet.

Figure 2:
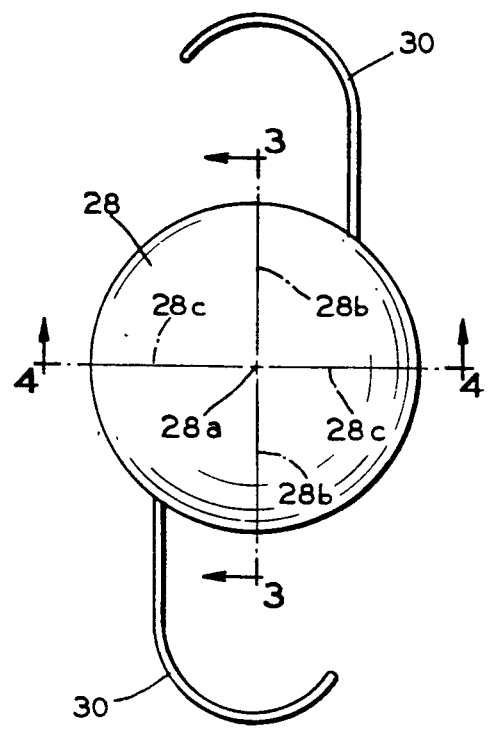
FIG. 2 is a front elevation view of a typical prior art intraocular lens.

Once the cataractous lens 20 has been surgically removed, light can be readily transmitted through the pupil 18 and toward the retina 22. However, the lens 20 performs a significant light focusing function. Consequently, with the lens 20 removed, the optical system of the eye is left about twenty diopters "short", and light is no longer properly focused on the retina 22. When a lens 20 is removed to eliminate cataracts, it must be replaced by an artificial lens. An intraocular lens, such as a prior art intraocular lens 28 shown in the FIG. 2, is commonly employed after cataract surgery to refocus the light on the retina 22.

Figure 5:
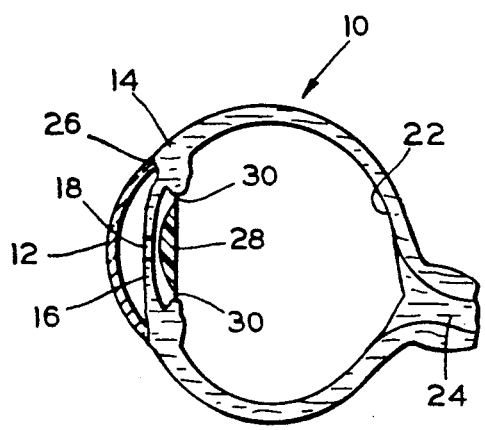
FIG. 5 is a cross-sectional side elevation view of the human eye shown in the FIG. 1 after the insertion of the intraocular lens shown in the FIG. 2.
Figure 6:
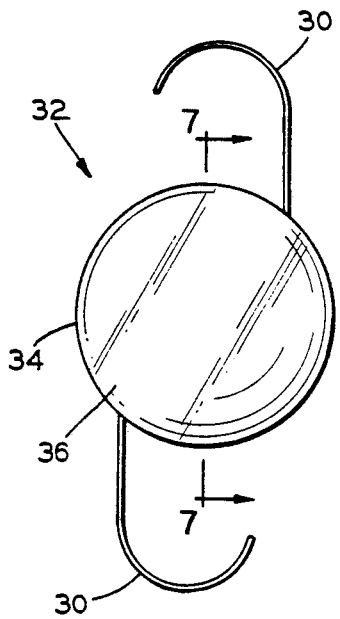
FIG. 6 is a front elevation view of an intraocular lens apparatus in accordance with the present invention.

The intraocular lens 28, which is constructed of any biologically inert, transparent material suitable for optical correction such as, for example, silicone, defines a toric section. The lens 28 is a section of a sphere, generally circular as viewed from the front with a diameter of approximately six millimeters. A pair of haptics 30 function as legs which support the lens 28 in the proper position in the posterior chamber of the eye 10 (FIG. 5). Each haptic 30 extends approximately four millimeters from a straight end attached to a periphery of the lens 28 to a curved end to be attached to the eye. Thus, the total width of the lens 28 and the haptics 30 is approximately fourteen millimeters.

The intraocular lens 28 is inserted behind the iris 16 as illustrated in the FIG. 5. This type of lens is referred to as a posterior chamber lens, the latest and most popular of the many designs of intraocular lenses.

It should be understood that the prior art lens 28 can be manufactured for positions in the eye other than the posterior chamber. For example, the lens 28 can be placed in the anterior chamber, the area intermediate the cornea 12 and the iris 16. However, such positioning is sometimes considered undesirable because positioning the lens very close to the cornea may result in traumatization of the endothelium.

A problem associated with the proper implantation of an intraocular lens is the accurate postoperative determination of the exact prescriptive or refracting power of the lens to be placed in the eye of the patient. The ophthalmologist can, for example, attempt to measure the prescriptive power of the natural lens 20 of the patient and, through the use of various measuring devices, e.g. ultrasound, measure the depth and diameter of the eye 10. These measurements in conjunction with clinical experience permit the ophthalmologist to relatively accurately determine the proper refraction or power of the intraocular lens 28 to be used.

In some cases however, despite the best efforts of the ophthalmologist, the lens surgically placed in the eye is not the correct dioptric power and the patient does not obtain good unaided visual acuity. During the postoperative healing period, the patient has a variable amount of astigmatism, a refracting defect which prevents focusing of sharp distinct images. Some astigmatism present after cataract surgery is due to the surgical incision and changes in corneal curvature as a consequence of the healing of the incision.

Figure 3:
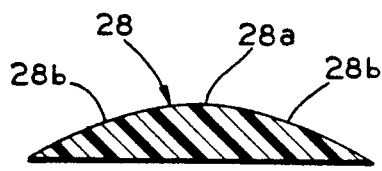
FIG. 3 is a cross-sectional view of the lens shown in the FIG. 2 taken along the line 3—3 on the vertical meridian.
Figure 4:
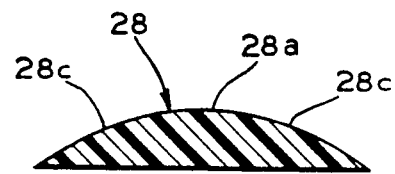
FIG. 4 is a cross-sectional view of the lens shown in the FIG. 2 taken along the line 4—4 on the horizontal meridian.

The curvature in the lens 28 can be formed asymmetric such that a vertical meridian, along a cross section line 3—3 as illustrated in the FIG. 3, is optically weaker than an horizontal meridian along a cross section line 4—4 as illustrated in the FIG. 4. The thickness of the lens 28 at a center 28a remains constant. Thus, the difference in the respective optical strengths of vertical and horizontal meridians is created by different structural contours (such as different radii of curvature), 28b and 28c, in the vertical and horizontal meridians respectively resulting in different light refracting characteristics. Thus, the lens 28 defines a toric section of a sphere. In order to properly align the lens 28 at the time of insertion in the eye, the haptics 30 are offset from and extend generally parallel to the vertical meridian.

Thus, as explained above, the prior art intraocular lens 28 has a fixed correction for astigmatism and a fixed power. In the FIGS. 6-9, there is shown a passive stable intraocular lens apparatus according to the present invention generally indicated by a reference numeral 32, which lens is provided with means for selectively changing the power of the lens and means for selectively providing correction for astigmatism. The lens apparatus 32 includes a transparent, flexible, generally circular envelope 34, formed of plastic or the like, surrounding and encasing a transparent gel 36 having a relatively high resistance to flow. The gel 36 can be a material such as silicone. A pair of the previously shown haptics 30 can be attached to the envelope 34. Although the envelope 34 of the lens assembly 32 has a convex surface facing toward the pupil 18 and a convex rear surface, it should be understood that the envelope 34 can be formed in other shapes as well. Typically, each of the front and rear surfaces will be one of concave, convex and plano in any of the nine possible combinations.

Figure 7:
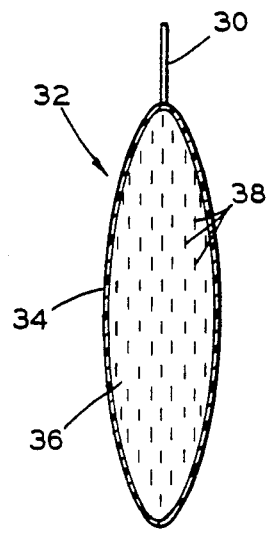
FIG. 7 is a cross-sectional view of the lens apparatus shown in the FIG. 6 taken along the line 7—7 illustrating a plurality of light refracting particles.

A plurality of spaced light refracting particles 38 are suspended within the gel 36. The particles 38 have a generally elongated shape in side view as shown in FIG. 7. The gel 36 maintains the particles 38 in a fixed position due to the high resistance to flow associated with the gel 36. The particles 38 are formed of a suitable material responsive to an external force having the capacity to rotate or change the orientation of the particles. For example, a first material, preferably solid, such as plastic, provides a light refractive body and is combined with a second material, such as a ferromagnetic material, which achieves a high degree of magnetic alignment in spite of the randomizing tendency of the thermal motions of the atoms. The ferromagnetic material can be any one of the five elements Iron, Cobalt, Nickel, Gadolinium and Dysprosium (Fe, Co, Ni, Gd and Dy), or a variety of alloys of these and other elements. The ferromagnetic material, because of the high degree of magnetic alignment, is responsive to an electromagnetic field. In some cases, the ferromagnetic material in the light refracting particles 38 can be "permanently" magnetized or simply temporarily aligned in response to the alignment of the electromagnetic field.

Figure 8:
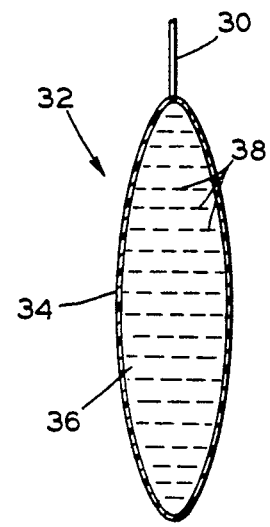
FIG. 8 is a cross-sectional view substantially similar to FIG. 7 illustrating the light refracting particles rotated 90°.

The particles 38 can be rotated to any degree of revolution. If the particles 38 are initially vertically disposed as shown in FIG. 7, the application of an electromagnetic field rotates each of the particles to a new position, for example a 90° change to a horizontal disposition as shown in FIG. 8. The degree to which the particles 38 are rotated can be varied by modifying the strength of the electromagnetic field, the distance of the electromagnetic field from the lens 32, and the time the electromagnetic field is applied.

Also, the particles can be selectively rotated. For example, a first predetermined number of the particles can be made to respond to a first force to functionally add about two and one half diopters of power to simulate accommodation to change focus from far to near. The patient could be provided with an instrument for making such a change without requiring the services of a doctor. Such a change could be stable after the instrument is removed or turned off, or could be temporary with the lens returning to the original setting when the first force is removed. A second predetermined number of the particles, which may or may not include the first predetermined number, may respond only to a second force which is applied by a doctor or other trained professional for greater power changes or changing the astigmatism correction.

The transparent particle material and the ferromagnetic material are combined in a manner sufficient to ensure that light entering the envelope 34 and passing through the gel 36 is refracted by the particles 38. For example, the ferromagnetic material can form a thin outer film surrounding the inner solid material. The ferromagnetic material is thin enough so as to be transparent, allowing the light to be refracted by the inner optically clear material. Alternatively, the ferromagnetic material can shaped into a form with an aperture in which the optically clear material is molded.

Figure 9:
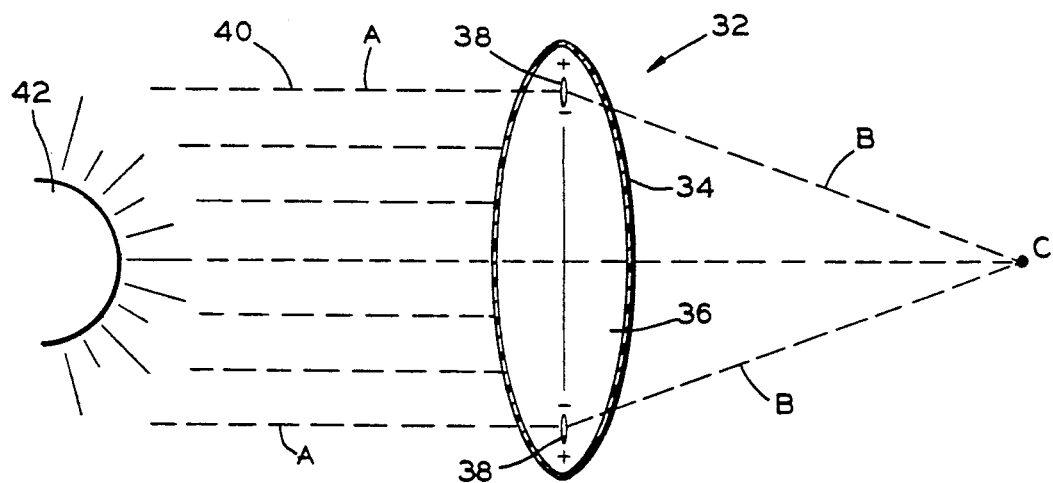
FIG. 9 is a schematic side elevation view of the intraocular lens apparatus according to the present invention illustrating two enlarged light refracting particles focusing beams from a light source.
Figure 10:
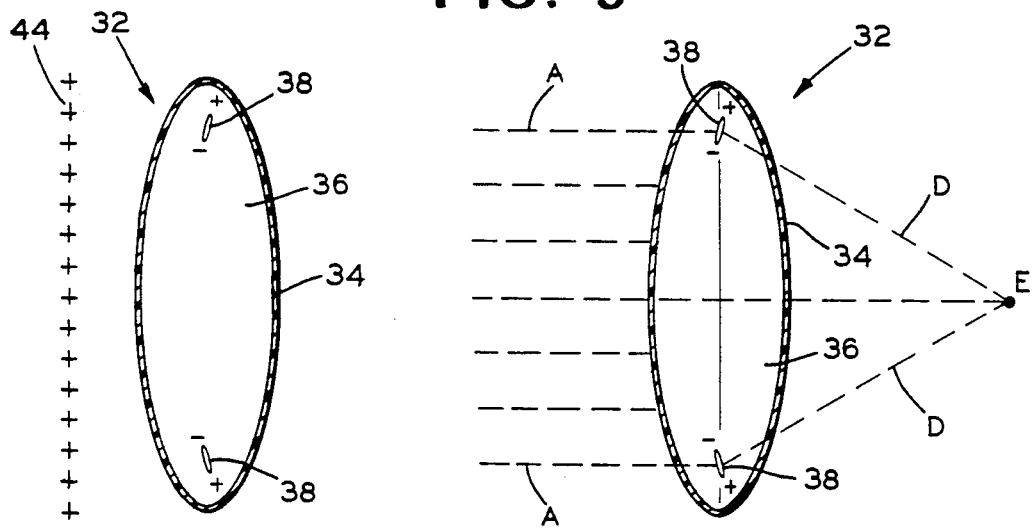
FIG. 10 is a view similar to FIG. 9 illustrating the light refracting particles rotated in a clockwise direction to an inclined position in the presence of a magnetic field.
Figure 11:
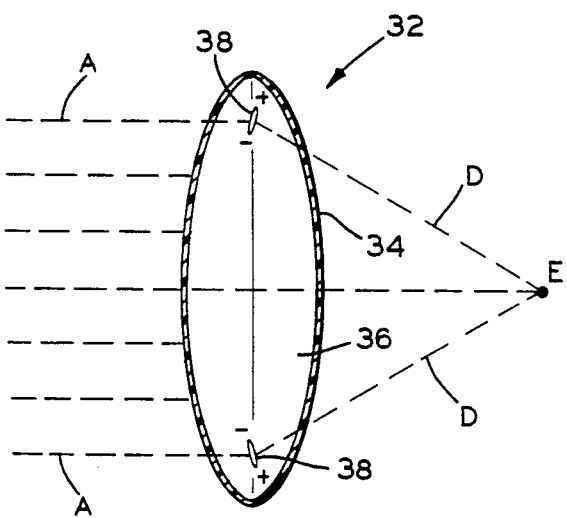
FIG. 11 is a view similar to FIG. 9 illustrating the light refracting particles rotated in a counterclockwise direction to an inclined position in the presence of an opposite polarity magnetic field.

The lens 32 is illustrated schematically in FIGS. 9-11 If the ferromagnetic material has previously been magnetized, the material will exhibit residual magnetism such that each of the light refracting particles 38 has a positively charged pole and a negatively charged pole as shown by the plus and minus symbols respectively. A pair of such particles 38 is shown in enlarged form in FIG. 9. The particles 38 are aligned longitudinally with a vertical axis of the lens 32 and the positive poles are oriented toward the periphery of the lens 32. When a positive polarity electromagnetic field is applied to one side of the lens 32, as shown in FIG. 10, a force is generated on the particles 38 along the magnetic lines of flux which are directed outwardly from the positively charged field in a generally horizontal path through the lens 32. The positive pole of each of the particles 38 is repelled by the magnetic field and the negative pole is attracted. Since the gel 36 has a high resistance to flow, the center of the particle 38 will remain in a fixed position within the gel while the edges of the particle rotate about the center. The electromagnetic field, by attracting one pole and repelling the other pole of the particle 38, effectuates a rotation or change in the orientation of the particle 38 as shown in FIG. 10.

The rotation of the particles 38 alters the index of refraction of the lens 32, thereby changing the power of the lens 32. As shown in FIG. 9, if refraction due to the shape of the envelope 34 is ignored for the purposes of illustration, light beams 40 from a light source 42 enter the variable focus intraocular lens 32 along a path A until contacting the light refracting particles 38. The particles 38 refract or bend the light beams 40 along a path B to a focal point C. Typically, the focal point C is the macula of the retina.

When a positively polarity electromagnetic field 44 is brought close to the lens 32, as shown in FIG. 10, the electromagnetic field 44 rotates the light refracting particles 38 to an inclined position by attracting the negative poles towards the field 44 and repelling the positive poles away from the field 44. The gel 36, because of the high resistance to flow, maintains the light refracting particles 38 in their rotated position after removal of the electromagnetic field 44. Thus, the changed characteristic of the lens is stable (maintained) and the stable condition is passive since it does not require the continued presence of the field which created it. It should be understood that a negative electromagnetic field can be used to rotate the light refracting particles 38 if the polarity of each of the particles is reversed.

As shown in FIG. 11, the light beams enter the lens 32 along the path A until contacting the light refracting particles 38. The inclined light refracting particles 38 refract the light beams 40 along a path D to a new focal point E. The focal point E is closer to the lens 32 than focal point C due to the greater refraction of the light and thus, the greater power of the lens. Therefore, as the particles are rotated, the refraction of the light increases and the power of the lens 32 is increased. Since the light refracting particles 38 can be rotated to a selected degree, the power of the lens 32 can be adjusted to any selected desired value and the power can be changed at any time. The lens 32 can be matched to the cornea after insertion in the eye and the power of the lens can be changed at a later time if the optics of the eye change.

Figure 12:
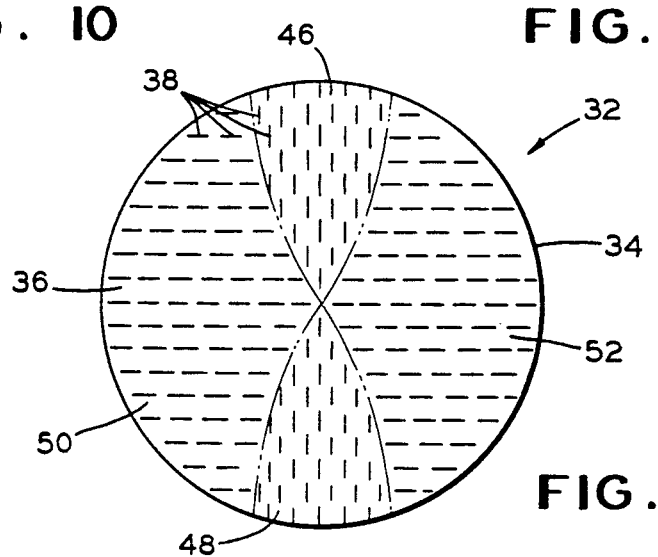
FIG. 12 is a front elevation view of the lens according to the present invention illustrating the subdivision of the light refracting particles for astigmatism correction.

The particles 38 can also be rotated for astigmatism correction. Subject to the limitations of focusing a magnetic field, each of the particles 38 can be oriented in a different direction from an adjacent one of the particles 38. The lens 32 can be subdivided into several areas each having a different orientation of the particles 38. For example, as shown in FIG. 12, the lens 32 is divided into four sectors or sections, 46, 48, 50, and 52. If the particles 38 in the diametrically opposed sections 46 and 48 are oriented for one Power and the particles in the diametrically opposed sections 50 and 52 are oriented for a different power, the lens 32 can be selectively set to correct for astigmatism which is aligned with the sections 46 and 48, for example.

An astigmatism located along any meridian of the eye 10 can be corrected by aligning the sections 46, 48, 50 and 52 through rotation about the center of the lens 32 as required The degree of the astigmatism is readily determinable through the use of conventional methods. The electromagnetic field 44 can then be applied to a predetermined area of the lens 32 to change the orientation of the particles 38 in that area.

The subdivision of the particles 38 into sections can be accomplished in many ways. For example, permanent magnets or current-carrying coils can be shaped to create electromagnetic fields having the desired shape. Also, a suitable electromagnetic shield, such as a ferromagnetic material of low resistivity, could be inserted between the lens 32 and the source of the field 44 to prevent rotation of all of the particles 38 except those in the selected area.

Figure 13:
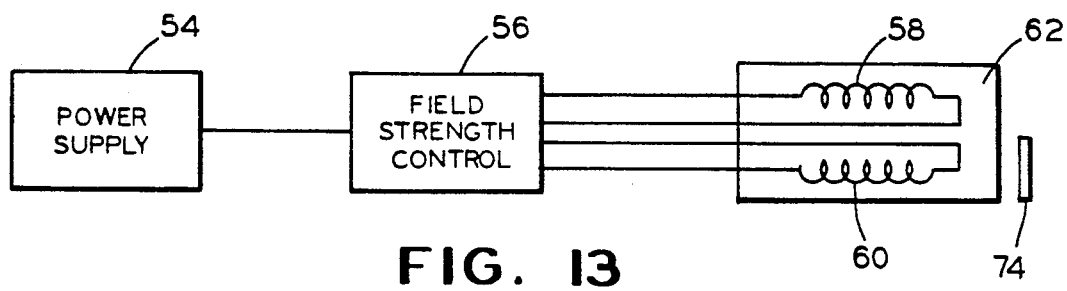
FIG. 13 is a schematic block diagram of a basic control apparatus for generating a magnetic field to rotate the light refracting particles in the lens according to the present invention.

There is shown in the FIG. 13 a block diagram of a control system for affecting the orientation of the light refracting particles 38 in the lens 32. A power supply 54 has an output connected to an input of a field strength control 56. An output of the field strength control 56 is connected to a first coil 58. A second output of the field strength control 56 is connected to a second coil 60. Each of the coils 56 and 60 can be mounted on a holder 62. The holder is any suitable device for positioning the coils 58 and 60 adjacent associated ones of the actuator bodies in any of the above-described lens assemblies. The field strength control 56 is selectively adjustable for applying a wide range of electrical power to each of the coils 58 and 60 individually in order to move the associated particles 38 in accordance to the selected inclinations. The coils 58 and 60 are representative of either a single coil or any other number of such coils as required to generate the desired electromagnetic field strength and shape.

Figure 14:
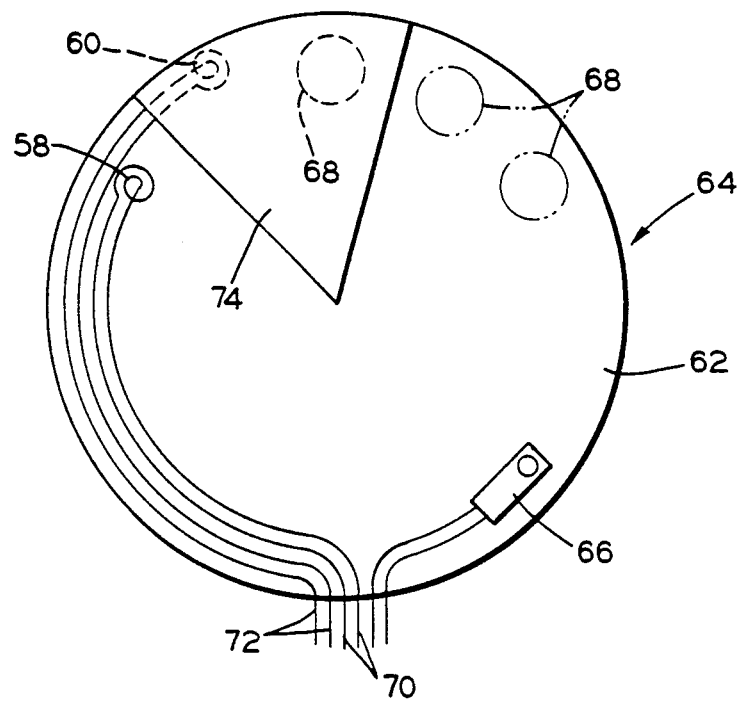
FIG. 14 is a front elevation view of an instrument used with the control apparatus shown in the FIG. 13.

As shown in the FIG. 14, the holder 62 can form a portion of an instrument generally indicated by reference numeral 64 for rotating the light refracting particles 38 of the lens 32. The holder 62, which can be disc-shaped has a suitable means utilized to align the instrument 64. For example, the holder 62 can be provided with a sight guide 66 such as an apparatus for projecting a laser beam at the lens and a viewing aperture for aligning the beam with a marking on the lens. Alternatively, the lens 32 can be provided with a marking visible only under ultraviolet or infrared light and the sight guide 66 would generate the required beam of light. Also mounted on the disc-shaped holder 62 are the coils 58 and 60, each of the coils being positioned for generating a portion of the required electromagnetic field. Additional coils 68 mounted on the holder 62 are shown schematically and represent any desirable number of such coils. The coil 58 is connected by a pair of lead wires 70 to any suitable control such as the field strength control 56 shown in FIG. 13. Similarly, the coil 60 is connected by a pair of lead wires 72 to a suitable control.

As shown in FIGS. 13 and 14, an electromagnetic shield 74 can be provided for shielding an area of the lens 32 from the electromagnetic field. For example, the shield 74 can be positioned between the coil 60 and the lens 32 (not shown) to prevent the particles 38 in a selected area of the lens from being rotated as the particles in the adjacent areas are being rotated by the electromagnetic field.

The instrument 64 can be incorporated into a device which can be utilized by the patient to change the shape of the lens body as the situation requires. For example, the instrument 64 can be built into a pair of eyeglasses or formed as a hand held control and operated by the patient to change the lens focus between near vision and far vision.

Figure 15:
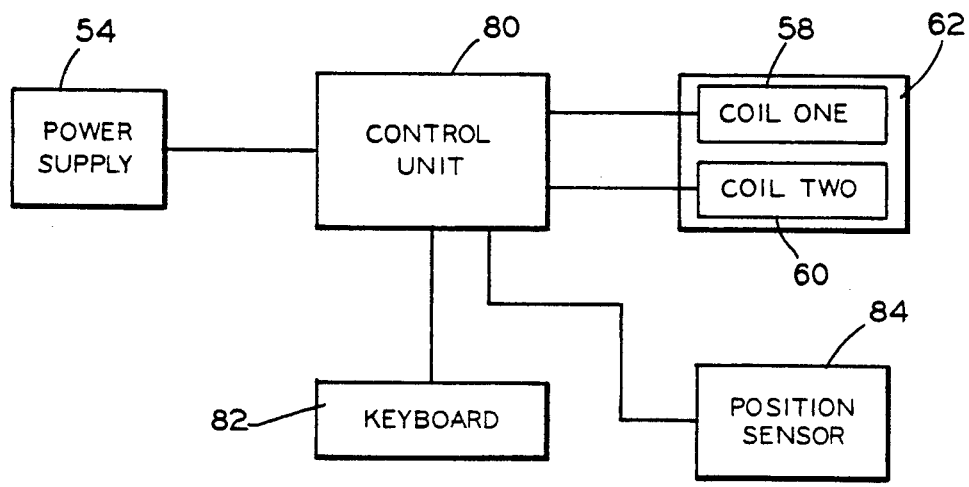
FIG. 15 is a schematic block diagram of an automated control apparatus for operating the instrument shown in the FIG. 14.

There is shown in the FIG. 15 a control for automatically changing the orientation of the light refracting particles 38 in the lens 32. The previously described power supply 54 is connected to an input of a control unit 80. A pair of outputs of the control unit 80 are connected to the coils 58 and 60 which are mounted on the holder 62. The control unit 80 can include a general purpose, programmed microprocessor having a standard operating software system and a program for receiving instructions through a keyboard 82 connected to an input of a control unit 80 as to the strength and duration of the electrical power to be applied from the power supply 54 to the coils 58 and 60 in order to generate the desired strength, duration and shape electromagnetic field. In addition, a position sensor 84 can be connected to an input of the control unit 80 for generating a signal representing the position of the holder 62 and the coils 58 and 60 with respect to the lens apparatus to be operated. The position sensor 84 can be any suitable device, typically light sensitive, for detecting any of the physical features on the lens apparatus. For example, the position sensor 84 could detect a marking on the envelope 34.

The utilization of such an intraocular lens in accordance with the present invention may eliminate the need of the recovering cataract patient to wear eye glasses or contact lenses. The elimination of the glasses or contact lenses amounts to an immense benefit to the recovering cataract patient, many of whom are elderly, sometimes forgetful, and many have financial and physical hardships. Furthermore, a source of the external force can be incorporated into a pair of eyeglasses, if needed, or a hand held device to be selectively operated by the patient for the accommodation of different focal lengths. The present invention has the advantage over prior art devices of not requiring a physical or electrical connection between the source of the power and the lens in order to change the lens. The variable focus lens of the present invention has a variety of applications, in addition to the application as an intraocular lens. For example, the variable focus lens can be used as a camera lens. The lens could be used as alternative to or in conjunction with cameras having either a fixed lens, an adjustable lens, or a plurality of interchangeable lenses.

Figure 16:
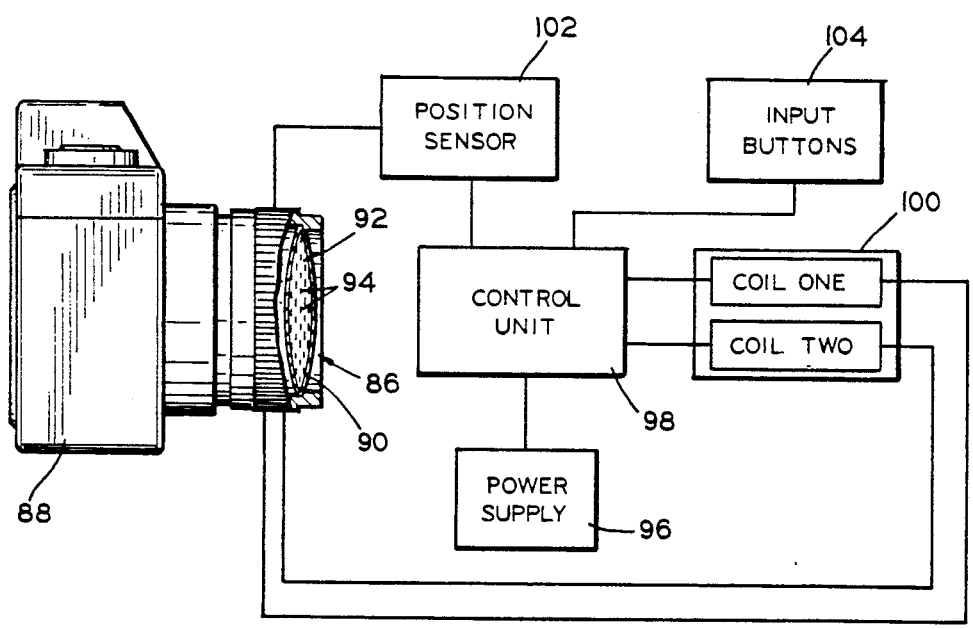
FIG. 16 is a schematic block diagram of an automated control apparatus for operating a camera utilizing a variable focus lens in accordance with the present invention.

There is shown in FIG. 16, a partial schematic and partial block diagram of a control system for operating a variable focus lens 86 in a camera 88. The variable focus lens apparatus 86 includes an optically clear, flexible, generally circular envelope 90 formed of plastic or the like, surrounding an optically clear gel 92 having a high resistance to flow. A plurality of spaced apart light refracting particles 94 are suspended in the gel 92. The gel 92 maintains the particles 94 in a fixed position due to the high resistance to flow. The particles 94 are formed of a suitable material responsive to an external force, for example, an optically clear material combined with a ferromagnetic material responsive to an electromagnetic field.

The control system for the camera 88 is substantially similar to the control system for the intraocular lens as described above. A power supply 96 has an output connected to an input of a field strength control unit 98. The control unit 98 has outputs to a coil arrangement 100, representative of either a single coil or plurality of coils, for generating an electromagnetic field. The control unit 98 also has an input from a position sensor 102 for proving a focus adjustment signal. The control unit 98 is responsive to a focus signal from input buttons 104. The control unit 98 changes the focus by controlling the strength of the electromagnetic field applied to the lens 86 and the time the electromagnetic field is applied to the lens 86. Alternatively, the control unit could adjust the position of the coil arrangement 100 relative to the lens 100.

The position sensor 102 or the input buttons 104 can be utilized to input commands to the control unit 98 to change the focus. For example, in a camera where the viewer does not look through the lens, the buttons can be utilized to input a signal proportional to the estimated distance to the subject. In a camera wherein the viewer looks through the lens, the position sensor can be connected to a focusing ring to generate the focus adjustment signal.

It should be understood the light refracting particles can be made of any suitable material which is responsive to an external force. For example, the light refracting particles can be composed of or coated with a suitable material which is responsive to vibrations caused by exposure to a particular ultrasonic frequency for rotating the particles. Additionally, the light refracting particles can be composed of a suitable material responsive to another form of energy such as a laser.

In summary, a variable focus means is provided to vary the power of a lens apparatus. The adjustable lens can be used in a variety of applications, for example, a camera lens or an intraocular lens for implantation into a human eye. When utilized as an intraocular lens, the variable focus lens can also be used to eliminate or reduce the effect of postoperative astigmatism that is induced during eye surgery. The invention utilizes an intraocular lens having an optically clear, flexible, generally circular envelope encasing the gel and a plurality of light refracting particles suspended in the gel. The light refracting particles are responsive to an external force for changing the orientation of the particles to a new position within the gel to adjust characteristics of the lens apparatus including the characteristics of power and astigmatism. The light refracting particles remain in the new position within the gel upon a removal f the external force because of the high resistance to flow of the gel which prevents the particles from changing position. The light refracting particles can be responsive to different types of external forces such as electromagnetic force fields, ultrasonic frequency emitting sources, and laser energy emitting sources.

In accordance with the provisions of the patent statutes, the present invention has been described in what is considered to represent its preferred embodiment. However, it should be noted that the invention can be practiced otherwise than as specifically illustrated and described without departing from its spirit or scope.

What is claimed is:

1. A passive stable variable focus intraocular lens apparatus, for implantation into an eye, comprising:
   a transparent, generally circular envelope;
   a transparent gel having a relatively high resistance to flow encased in said envelope; and
   a plurality of light refracting particles suspended in a predetermined orientation in said gel, said particles being responsive to an external force for changing to a new orientation of said particles with respect to said envelope for selectively adjusting characteristics of said lens apparatus including the characteristics of power and astigmatism correction, whereby upon removal of the external force, said particles remain in said new orientation within said gel.

2. The lens apparatus according to claim 1 wherein said envelope is formed as an outer surface of said gel.

3. The lens apparatus according to claim 1 wherein said envelope is formed of plastic material.

4. The lens apparatus according to claim 1 wherein said light refracting particles are responsive to an electromagnetic external force for changing the orientation of said particles to a new position within said gel.

5. The lens apparatus according to claim 1 wherein said light refracting particles include a ferromagnetic material.

6. The lens apparatus according to claim 1 wherein said light refracting particles are formed of a ferromagnetic material and a plastic material.

7. The lens apparatus according to claim 1 wherein said light refracting particles are formed of a transparent material coated with a ferromagnetic material.

8. The lens apparatus according to claim 1 wherein said envelope has one of a convex, concave and plano surface facing a pupil of an eye and one of a convex, concave and plano rear surface.

9. A passive stable variable focus lens apparatus comprising:
   a transparent, generally circular envelope;
   a transparent gel having a relatively high resistance to flow encased in said envelope;
   a plurality of light refractive particles suspended in a predetermined orientation in said gel; and
   means for generating an electromagnetic field, said particles being responsive to an external force applied by the electromagnetic field for changing to a new orientation of said particles with respect to said envelope for selectively adjusting characteristics of said lens apparatus including the characteristics of power and astigmatism correction, whereby upon removal of the external force, said particles remain in said new orientation within said gel.

10. The lens apparatus according to claim 9 wherein said light refracting particles include a ferromagnetic material.

11. The lens apparatus according to claim 9 wherein said light refracting particles are formed of a ferromagnetic material and a plastic material.

12. The lens apparatus according to claim 9 wherein said light refracting particles are formed of a transparent material coated with a ferromagnetic material.

13. The lens apparatus according to claim 9 including a first area in said gel having a first plurality of said light refracting particles in a first orientation and a second area in said gel having a second plurality of said light refracting particles in a second orientation whereby the lens apparatus corrects for astigmatism.

14. The lens apparatus according to claim 9 including an electromagnetic shield for shielding a selected area of said gel from the electromagnetic field generated by said means for generating said electromagnetic field.

15. The lens apparatus according to claim 14 wherein said electromagnetic shield is formed of a material having a relatively low resistivity.

16. The lens apparatus according to claim 9 wherein said means for generating an electromagnetic field includes a sight guide for aligning said means for generating an electromagnetic field with said envelope.

17. The lens apparatus according to claim 9 including a control system for controlling at least one of the strength and duration of the electromagnetic field applied to said particles.

18. A passive stable variable focus lens apparatus comprising:
   a transparent, generally circular envelope;
   a transparent gel having a relatively high resistance to flow encased in said envelope;
   a plurality of light refractive particles suspended in a predetermined orientation in said gel;
   means for generating a force field; and
   a control system for controlling at least one of the strength and duration of the force field applied to said particles connected to said means for generating a force field, said particles being responsive to an external force applied by the force field for changing to a new orientation of said particles with respect to said envelope for selectively adjusting characteristics of said lens apparatus including at least one of the characteristics of power and astigmatism correction, whereby upon removal of the external force, said particles remain in said new orientation within said gel.

19. The lens apparatus according to claim 18 including means connected to said control means for generating an adjustment signal, said control means being responsive to said adjustment signal for applying the force field to said particles.

20. The lens apparatus according to claim 19 wherein said light refracting particles are formed of a ferromagnetic material and a plastic material and said force field is an electromagnetic field.

* * * * *